(12) United States Patent
Franke et al.

(10) Patent No.: US 9,950,113 B2
(45) Date of Patent: Apr. 24, 2018

(54) NEEDLE ASSEMBLY FOR THE DELIVERY OF AT LEAST TWO MEDICAMENTS

(75) Inventors: Beate Franke, Frankfurt am Main (DE); Zdenek Cerman, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 60 days.

(21) Appl. No.: 13/881,977

(22) PCT Filed: Oct. 31, 2011

(86) PCT No.: PCT/EP2011/069109
§ 371 (c)(1),
(2), (4) Date: Apr. 26, 2013

(87) PCT Pub. No.: WO2012/059460
PCT Pub. Date: May 10, 2012

(65) Prior Publication Data
US 2013/0267932 A1    Oct. 10, 2013

Related U.S. Application Data

(60) Provisional application No. 61/432,719, filed on Jan. 14, 2011.

(30) Foreign Application Priority Data

Nov. 3, 2010  (EP) .................................... 10189807

(51) Int. Cl.
*A61M 5/19* (2006.01)
*A61M 5/24* (2006.01)
(Continued)

(52) U.S. Cl.
CPC ............ *A61M 5/19* (2013.01); *A61M 5/2448* (2013.01); *A61M 5/3294* (2013.01); *A61M 5/284* (2013.01);
(Continued)

(58) Field of Classification Search
CPC .............. A61M 5/31596; A61M 5/284; A61M 5/2448; A61M 2005/3128; A61M 5/2033;
(Continued)

(56) References Cited

U.S. PATENT DOCUMENTS

| 533,575 A | 2/1895 | Wilkens |
|---|---|---|
| 5,226,895 A | 7/1993 | Harris |

(Continued)

FOREIGN PATENT DOCUMENTS

| EP | 0937471 A2 | 8/1999 |
|---|---|---|
| EP | 0937476 A2 | 8/1999 |

(Continued)

OTHER PUBLICATIONS

English Translation of Notice of Reason of Rejection issued in Japanese Patent Application No. 2013-537105 dated Aug. 21, 2015.
(Continued)

*Primary Examiner* — Bhisma Mehta
*Assistant Examiner* — Larry R Wilson
(74) *Attorney, Agent, or Firm* — McDonnell Boehnen Hulbert & Berghoff LLP

(57) ABSTRACT

Various embodiments of needle assemblies for use with a drug delivery device to deliver two or more medicaments are provided. Additionally, various embodiments of methods for delivering two or medicaments are provided. In one embodiment, a needle assembly comprises an injection needle, a proximal housing member, a distal housing member, and a medicament transfer element. The proximal housing member contains a first medicament and is configured to attach to a drug delivery device containing a second medicament. The distal housing member is movably engaged with the proximal housing member such that relative axial movement between the proximal and distal housing members causes the first medicament to be delivered. Upon activation of the
(Continued)

drug delivery device (e.g., activation of a dose button of the drug delivery device) the second medicament is transferred, via the medicament transfer feature, from the drug delivery device to the injection needle of the needle assembly such that the second medicament can be delivered.

13 Claims, 7 Drawing Sheets

(51) Int. Cl.
*A61M 5/28* (2006.01)
*A61M 5/315* (2006.01)
*A61M 5/32* (2006.01)
*A61M 5/34* (2006.01)
*A61M 5/50* (2006.01)
*A61M 5/178* (2006.01)
*A61M 5/31* (2006.01)

(52) U.S. Cl.
CPC ......... *A61M 5/31596* (2013.01); *A61M 5/326* (2013.01); *A61M 5/347* (2013.01); *A61M 5/50* (2013.01); *A61M 5/5086* (2013.01); *A61M 2005/1787* (2013.01); *A61M 2005/3128* (2013.01); *A61M 2005/3247* (2013.01); *A61M 2005/3267* (2013.01)

(58) Field of Classification Search
CPC .......... A61M 5/3202; A61M 2005/287; A61M 2005/1787; A61M 5/19; A61M 5/3294; A61M 5/326; A61M 5/3295; A61M 2005/3247
USPC ............ 604/82–92, 184, 200–206, 411–416
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,876,372 A * | 3/1999 | Grabenkort et al. | 604/89 |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,526,002 B1 | 5/2003 | Taylor | |
| 6,743,203 B1 | 6/2004 | Pickhard | |
| 6,899,698 B2 | 5/2005 | Sams | |
| 6,936,032 B1 | 8/2005 | Bush, Jr. et al. | |
| 7,241,278 B2 | 7/2007 | Moller | |
| 2001/0037087 A1 | 11/2001 | Knauer | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0229562 A1 * | 10/2006 | Marsh | A61M 5/204 604/164.01 |
| 2006/0276755 A1 | 12/2006 | Sullivan et al. | |
| 2009/0275916 A1 | 11/2009 | Harms et al. | |

FOREIGN PATENT DOCUMENTS

| | | | |
|---|---|---|---|
| FR | 1320820 A | 3/1963 | |
| JP | S57-120033 U | 7/1982 | |
| JP | 2008535636 A | 9/2008 | |
| WO | 9938554 A1 | 8/1999 | |
| WO | 0110484 A1 | 2/2001 | |
| WO | 2007027203 A2 | 3/2007 | |
| WO | WO 2010139672 A1 * | 12/2010 | A61M 5/284 |

OTHER PUBLICATIONS

Form PCT/IPEA/416, Notification of Transmittal of the International Preliminary Report on Patentability, dated Mar. 5, 2013.

* cited by examiner

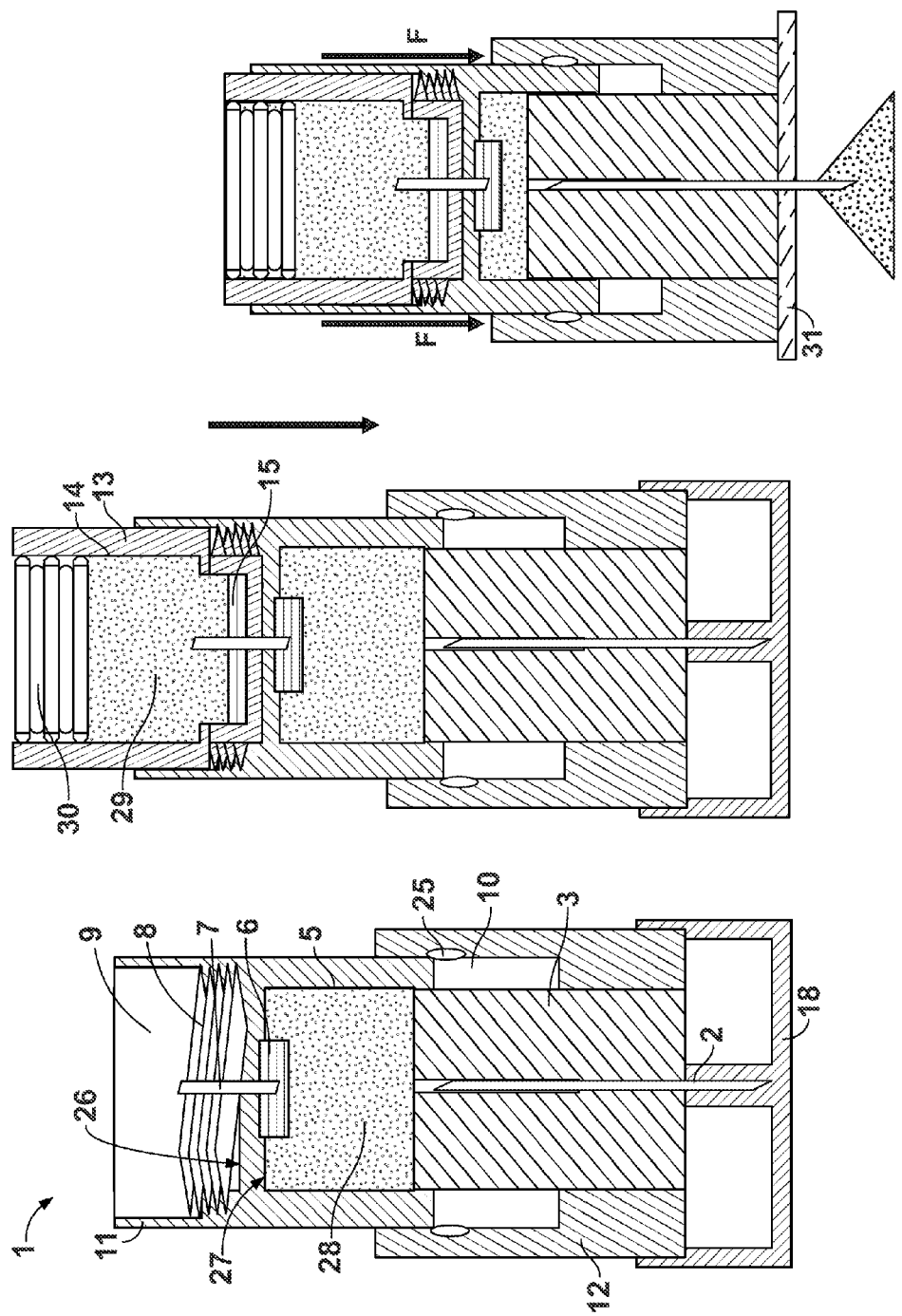

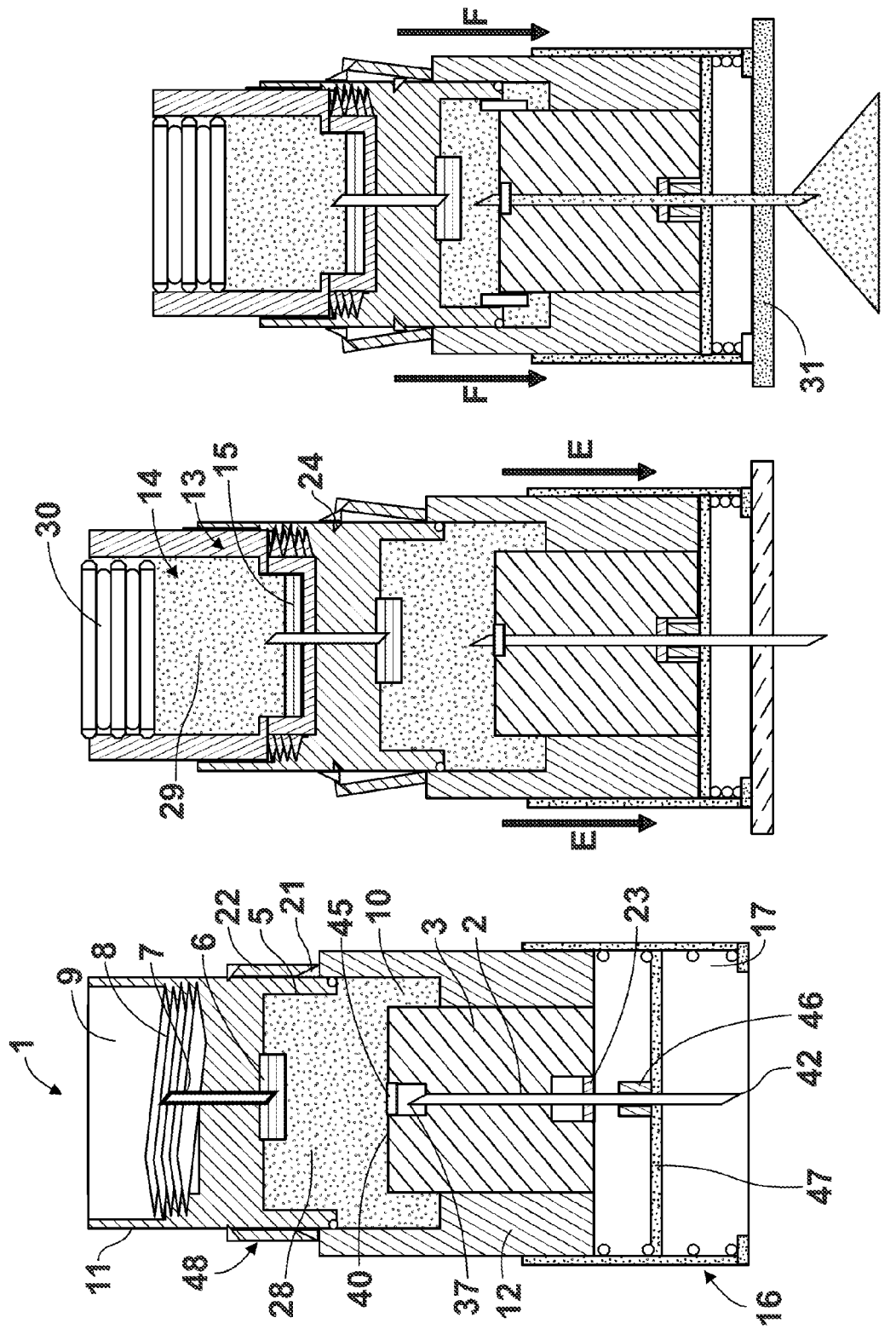

NEEDLE ASSEMBLY FOR THE DELIVERY OF AT LEAST TWO MEDICAMENTS

CROSS REFERENCE TO RELATED APPLICATIONS

The present application is a U.S. National Phase Application pursuant to 35 U.S.C. § 371 of International Application No. PCT/EP2011/069109 filed Oct. 31, 2011, which claims priority to European Patent Application No. 10189807.0 filed Nov. 3, 2010 and U.S. Provisional Patent Application No. 61/432,719 filed Jan. 14, 2011. The entire disclosure contents of these applications are herewith incorporated by reference into the present application.

FIELD OF INVENTION

This present patent application relates to medical devices and methods using such devices for delivering at least two drug agents (or medicaments) to a patient (or user), wherein the devices have a single dose setting mechanism and a single dispense interface. A delivery procedure initiated by the user causes a non-user settable dose of a first drug agent and a variable set dose of a second drug agent to be delivered to the patient. The drug agents may be available in two or more reservoirs, chambers, containers or packages, each containing independent (single drug compound) or pre-mixed (co-formulated multiple drug compounds) drug agents.

BACKGROUND

Certain disease states require treatment using one or more different drug agents. Some drug compounds need to be delivered in a specific relationship with each other in order to deliver the optimum therapeutic dose. The presently proposed devices and methods are of particular benefit where combination therapy is desirable, but not possible in a single formulation for reasons such as, but not limited to, stability, compromised therapeutic performance, and toxicology. For example, in some cases it might be beneficial to treat a diabetic with long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems associated with the storage and simultaneous delivery of two or more active drug agents. For instance, if the two active agents are stored for an extended period of time in the same chamber, then they may interact with each other. Therefore, it may advantageous to store the active components separately and combine them at the point of delivery (e.g., during injection, needle-less injection or inhalation). However, the process for combining the two drug agents needs to be simple and convenient for the user to perform reliably, repeatedly, and safely.

A further problem is that the quantities and/or proportions of each active drug agent making up the combination therapy may need to be varied for each user or at different stages of therapy. For example, one or more active agents may require a titration period to gradually introduce a patient up to a "maintenance" dose. A further example would be if one active agent requires a non-adjustable fixed dose while the other is varied in response to a patient's symptoms or physical condition. Accordingly, pre-mixed formulations of multiple active drug agents may not be suitable as these pre-mixed formulations would have a fixed ratio of the active components, which could not be varied by the healthcare professional or user.

Additional problems arise where a multi-drug compound therapy is required because many users cannot cope with having to use more that one drug delivery system or make the necessary accurate calculation of the required dose combination. This is especially true for users with dexterity or computational difficulties. In some circumstances it is also necessary to perform a priming procedure of the device and/or needle cannula before dispensing the drug agents.

In light of the foregoing, it is desirable to provide user-friendly devices and methods for the delivery of two or more drug agents.

SUMMARY

Disclosed herein are various embodiments of needle assemblies for use with a drug delivery device (collectively referred to as a "drug delivery system") to deliver two or more drug agents (or medicaments), as well as various methods making use of such needle assemblies. The presently proposed needle assemblies and methods allow for the delivery of complex combinations of multiple drug compounds using a single drug delivery system. Further, the presently proposed needle assemblies and methods allow a user to set and dispense at least two medicaments using drug delivery systems having only a single dose setting mechanism and a single dispense interface. A single dose setter can control the dose setting mechanism of the drug delivery system such that a predefined combination of the individual drug compounds is delivered when a single dose of one of the medicaments is set and dispensed through the single dispense interface.

A needle assembly according to the invention may comprise a first medicament. The first medicament may be contained in the proximal housing member.

The first medicament may be contained in a reservoir or first medicament chamber in the needle assembly. The needle assembly may be pre-filled with the first medicament. "Pre-filled" in this regard means that the needle assembly is filled with the first medicament already before the needle assembly is attached to a drug delivery device. The needle assembly may therefore be pre-filled with the first medicament before fluid communication is established between the needle assembly and the drug delivery device.

The needle assembly may be self-contained and may be provided as a sealed and sterile disposable module. Although not shown, the needle assembly could be contained in a protective and sterile capsule or container. The needle assembly could then be supplied by a manufacturer where the user would peel or rip open a seal or the container itself to gain access to a sterile needle assembly. In some instances it might be desirable to provide two or more seals for each end of the needle assembly. The seals may ensure integrity of the first medicament contained within the needle assembly. The seals may ensure that no medicament is lost during storage time, or that medicament is not contaminated, e.g. with humidity.

The drug delivery device may comprise a reservoir or container that is at least partly filled with a second medicament before the needle assembly is attached to the device.

By defining a therapeutic relationship (or therapeutic profile) between the individual drug compounds, the proposed needle assemblies and methods making use of such assemblies help ensure that a patient (or user) receives an optimum therapeutic dose combination of multiple drug compounds from a drug delivery system without the inherent risks associated with multiple inputs where the user has to calculate and set the correct dose combination every time they use the system. Accordingly, drug delivery systems incorporating the proposed needle assemblies are of particular benefit to users with dexterity or computational difficulties.

A needle assembly according to the invention may comprise an injection needle, a proximal housing member, a distal housing member, and a medicament transfer feature.

The proximal housing member may contain a first medicament. The proximal housing member may comprise a reservoir containing a first medicament. The reservoir may be a medicament chamber containing the first medicament. The proximal end of the reservoir may be defined by the proximal housing member. The distal end of the reservoir may be defined by the distal housing member. The distal end of the reservoir may be defined by a bung, e.g. a movable bung. The distal end of the reservoir may be defined by a needle hub attached to the distal housing member.

The proximal housing member may be configured to attach, for example via a threaded engagement, to a drug delivery device containing a second medicament. The drug delivery device may contain the second medicament prior to attachment. The needle assembly may contain the first medicament prior to attachment. The injection needle may be arranged at the distal end of the needle assembly, in particular at the distal housing member.

The medicament transfer feature may be in one of two statuses. The medicament transfer feature may be configured to switch state. In the first or initial state, the medicament transfer feature may be configured to prevent fluid communication between the first medicament in the needle assembly and the second medicament in the drug delivery device. The medicament transfer feature may be configured to prevent fluid communication between the first medicament in the needle assembly and the second medicament in the drug delivery device during a first delivery step when the first medicament from the medicament chamber in the needle assembly is delivered. The first medicament may be delivered through the injection needle. In the second state the medicament transfer feature may be configured for transferring the second medicament from the drug delivery device to the injection needle of the needle assembly during activation of the drug delivery device such that the second medicament can be delivered. When the drug delivery device is activated, the medicament transfer feature may be in the second state, wherein the medicament transfer feature may be configured for transferring the second medicament from the drug delivery device to the injection needle of the needle assembly during activation of the drug delivery device such that the second medicament can be delivered in a second delivery step. The second medicament may be delivered through the injection needle.

The medicament transfer feature may further comprise a transfer sealing member. The transfer sealing member may prevent fluid communication between the first medicament and the second medicament. The transfer sealing member may be closed or intact when the medicament transfer feature is in the first state. The transfer sealing member may be open or broken or pierced when the medicament transfer feature is in the second state.

The distal housing member may be movably engaged, e.g., slidably engaged, with the proximal housing member such that relative axial movement of the proximal housing member towards the distal housing member may cause the first medicament to enter the injection needle and ultimately to be delivered to a user. The relative axial movement of the proximal housing member towards the distal housing member may cause the volume of the reservoir containing the first medicament to be reduced. The relative axial movement or telescopic movement of the proximal and distal housing members may compress the reservoir containing the first medicament and may cause the medicament to enter the injection needle and to be delivered to a user. This movement may cause the first medicament to be displaced out of the reservoir through the injection needle.

In one embodiment, a needle assembly comprises an injection needle, a proximal housing member, a distal housing member, and a medicament transfer feature. The proximal housing member contains a first medicament and is configured to attach, perhaps via a threaded engagement, to a drug delivery device containing a second medicament. The distal housing member is movably engaged (e.g., slidably engaged) with the proximal housing member such that relative axial movement between the proximal and distal housing members causes the first medicament to enter the injection needle and ultimately to be delivered to a user. Upon activation of the drug delivery device (e.g., activation of a dose button of the drug delivery device) the second medicament is transferred, via the medicament transfer feature, from the drug delivery device to the injection needle of the needle assembly such that the second medicament can be delivered to the user. It should be understood that the delivery of the first and second medicaments is done via the same injection needle and further that the delivery of both medicaments may be done in one continuous injection step or in multiple injection steps. One injection step offers a convenient benefit to the user in terms of reduced user steps compared to administering two separate injections. This convenience benefit may also result in improved compliance with the prescribed therapy, particularly for users who find injections unpleasant or who have computational or dexterity difficulties. The drug delivery device may be a multiple dose delivery device such that it contains a cartridge having multiple doses of the second medicament (e.g., insulin) while a single dose of a first medicament may be contained in the proximal housing member of the needle assembly.

The needle assembly may comprise various additional components. For example, the needle assembly may comprise an injection needle hub attached to the distal housing member. The injection needle may be coaxially fixed within the injection needle hub. In another example, the needle assembly may further comprise an injection needle shield for preventing inadvertent contact between the distal end of the injection needle and a user. The injection needle shield may be connected to the distal housing member, and may be proximally retractable. In another example, the needle assembly may further comprise a locking mechanism, such as at least one cam lock, for preventing inadvertent relative axial movement between the proximal and distal housing members. In yet another example, the needle assembly may further comprise an injection needle sealing cap that is removably attached to either the distal housing member or to the distal end of the injection needle.

The medicament transfer feature may comprise various components. The medicament transfer feature may comprise a transfer needle. The medicament transfer feature may comprise a transfer sealing member. For example, the medicament transfer feature may comprise a transfer needle and a transfer sealing member. The transfer sealing member may comprise an unidirectional valve, wherein fluid pressure induced during activation of the drug delivery device causes the valve to open. In another example, the transfer sealing member may comprise a sealing surface pierceable by a proximal end of the injection needle. The transfer sealing member may prevent fluid communication between the first medicament and the second medicament. The transfer sealing member may provide for sterility of the medicament contained in the needle assembly.

The transfer needle may be configured to establish fluid communication between the needle assembly and the second medicament in the drug delivery device. The transfer needle may be configured to pierce a piercable septum that seals a container in a drug delivery device. The transfer needle may provide a channel configured to establish fluid communication between the needle assembly and the second medicament in the drug delivery device. The transfer needle may alternatively be part of the drug delivery device.

In another embodiment, a needle assembly comprises an injection needle, a proximal housing member, a distal housing member, a medicament transfer element, and an injection needle hub. The proximal housing member includes a first medicament chamber containing a first medicament and is configured to attach, perhaps via a threaded engagement, to a drug delivery device containing a second medicament. The distal housing member is movably engaged with the proximal housing member such that relative axial movement between the proximal and distal housing members causes the first medicament to enter the injection needle and to be delivered to a user. Upon activation of the drug delivery device the second medicament is transferred, via the medicament transfer feature, from the drug delivery device to the injection needle of the needle assembly such that the second medicament can be delivered to the user. The injection needle hub is attached to the distal housing member, and the injection needle is fixed, perhaps coaxially, within the injection needle hub.

The needle assembly may further comprise an axially moveable bung positioned at least partially within the first medicament chamber, where the distal end of the first medicament chamber may be sealed by the moveable bung. The moveable bung may comprise (i) a pierceable portion pierceable by the proximal end of the injection needle and (ii) a sealing portion.

In this embodiment, a first relative axial movement between the proximal and distal housing members results in the proximal end of the injection needle piercing the pierceable portion of the moveable bung, and a second relative axial movement between the proximal and distal housing members results in the moveable bung moving in the proximal direction, thus forcing the first medicament to enter the injection needle and to be delivered to the user. The first and second relative axial movements may occur as one continuous motion.

In one embodiment of a method using a needle assembly for delivering at least two medicaments, the method comprises (i) providing a needle assembly comprising an injection needle, a proximal housing member containing a first medicament, and a distal housing member slidably engaged with the proximal housing member, (ii) attaching the needle assembly to a drug delivery device containing a second medicament, (iii) inserting the injection needle into a user; (iv) axially moving the proximal and distal housing members of the needle assembly relative to one another such that the first medicament is delivered to the user, and (v) activating the drug delivery device such that the second medicament is delivered to the user. It should be understood that the delivery of the first and second medicaments may be done in one continuous injection step. It should be understood that the method may use a needle assembly according to the embodiments disclosed herein. It should be understood that the method may use a needle assembly wherein the needle assembly further comprises a medicament transfer feature for transferring the second medicament from the drug delivery device to the injection needle of the needle assembly during activation of the drug delivery device such that the second medicament can be delivered to the user. Further the method my use a needle assembly, wherein the medicament transfer feature comprises a transfer needle and a transfer sealing member comprising a unidirectional valve, and wherein fluid pressure induced during activation of the drug delivery device causes the unidirectional valve to open.

A needle assembly as presently proposed may be designed for use with any drug delivery device with an appropriate compatible interface. However, it may be preferable to design the needle assembly in such a way as to limit its use to one exclusive primary drug delivery device (or family of devices) through employment of dedicated or coded features to prevent attachment of a non-appropriate needle assembly to a non-matching device. In some situations it may be beneficial to ensure that the needle assembly is exclusive to one drug delivery device while also permitting the attachment of a standard drug dispense interface to the device. This would allow the user to deliver a combined therapy when the needle assembly is attached, but would also allow delivery of a primary compound independently through a standard drug dispense interface in situations, such as, but not limited to, dose splitting or top-up of the primary compound. The needle assembly may further comprise features that prevent reattachment to a primary drug delivery device or that prevent or discourage subsequent dosing through the needle via alternative means. For example, the needle assembly may include a locking needle guard that is activated after a user delivers a dose from the needle assembly. Additionally, the needle assembly may comprise one or more additional features for:

Physical prevention of needle assembly re-attachment to the primary drug delivery device once the needle assembly has been used and removed.

Physical/hydraulic prevention of subsequent liquid flow through the drug dispense interface once it has been used.

Visual warnings (e.g., change in color and/or warning text/indicia within an indication window on the needle assembly once insertion and/or fluid flow has occurred).

Tactile feedback (e.g., presence or absence of tactile features on the outer surface of the needle assembly following use).

The drug delivery device may be a multi-use device or a single use disposable device. Further, the drug delivery device may or may not have a replaceable cartridge (or reservoir/chamber). It is also possible to have a set of different needle assemblies for various conditions that could be prescribed as one-off extra medication to patients already using a standard drug delivery device.

Herein, medicaments may be fluids, defined as liquids, gases or powders that are capable of flowing and that change shape at a steady rate when acted upon by a force. The medicaments may be a solid that is carried, solubilized or otherwise dispensed with another fluid medicament. Further, it should be understood that a single medicament (e.g., a first medicament) may comprise a combination of drug agents. Even further, a reference herein to a single medicament (e.g., transferring a second medicament) may refer to a single dose or multiple doses of a single drug agent or a combination of drug agents. In one example, a medicament may be a master drug compound, such as insulin. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs may be used.

Herein, the term "insulin" shall mean insulin, insulin analogs, insulin derivatives or mixtures thereof, including human insulin or a human insulin analogs or derivatives. Examples of insulin analogs are, without limitation, Gly (A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyhepta-decanoyl) human insulin.

As used herein, the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly- Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Examples of Hormones, without limitation, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

The above-mentioned aspects will become apparent to those of ordinary skill in the art by reading the following detailed description, with appropriate reference to the accompanying drawings. Further, it is expressly contemplated that any alternative, permutation, or other variation or feature of any disclosed embodiment may apply to any other embodiment, to the extent that the alternative, permutation, or other variation or feature would be consistent and compatible with such other embodiment. In other words, disclosure of a given alternative, permutation, or other variation or feature of a needle assembly or method of using such an assembly, and/or any other component or collection of components in connection with a given embodiment thereof is in no way intended to be limited to that given embodiment. Furthermore, it should be noted that the above overview is intended to be illustrative and not limiting.

BRIEF DESCRIPTION OF THE DRAWINGS

Exemplary embodiments are described herein with reference to the following drawings, wherein like numerals denote like entities:

FIG. 1a is a cross-sectional view of an exemplary needle assembly;

FIG. 1b is a cross-sectional view of the needle assembly of FIG. 1a connected to an exemplary drug delivery device;

FIG. 1c is a cross-sectional view of the needle assembly of FIG. 1b during a first delivery step;

FIG. 5a is a cross-sectional view of another exemplary needle assembly having a needle shield;

FIG. 5b is a cross-sectional view of the needle assembly of FIG. 5a connected to an exemplary drug delivery device;

FIG. 5c is a cross-sectional view of the needle assembly of FIG. 5b during a first delivery step;

DETAILED DESCRIPTION

Figure 2A:
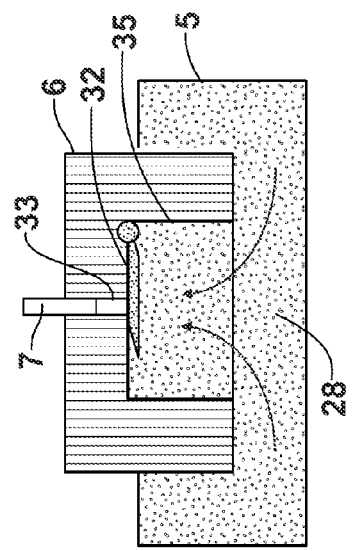
FIG. 2a is a detailed cross-sectional view of an exemplary medicament transfer sealing member of the needle assembly of FIG. 1b during a first delivery step, where the transfer sealing member comprises a valve.

Generally, needle assemblies comprise a needle, a needle hub, and an outer sleeve with a means for connecting the needle assembly to a drug delivery device (or pen injection device). Once connected, the needle pierces a septum of a medicament cartridge (or reservoir/chamber) in the drug delivery device and delivery of a single medicament is enabled. However, under certain circumstances may be desirable to provide devices and methods for the delivery of two or more medicaments.

In FIG. 1a, a cross-sectional view of an exemplary embodiment of a needle assembly 1 for the delivery of at least two medicaments is shown. The needle assembly 1 is divided into two major components: a proximal housing member 11 and a distal housing member 12. As shown, both housing members 11, 12 are movably engaged such that they can slide relative to one another. Securing members 25 prevent inadvertent relative axial movement between the proximal and distal housing members 11, 12. Each securing member 25 may comprise a cam lock or another type of protrusion mechanism.

The proximal housing member 11 comprises a mounting portion 9 including threads 8 for attaching the needle assembly 1 to a drug delivery device. Other embodiments may include various other attachment means such as a snap or ratchet mechanism. As shown, a transfer needle 7 is located coaxially inside the mounting portion 9 and protrudes from the distal wall 26 of the mounting portion 9. Although the transfer needle 7 is shown to be located coaxially inside the mounting portion 9, it may not be coaxially located in other embodiments. The proximal housing member 11 also includes a first medicament chamber 5 containing a first medicament 28. The distal end of the first medicament chamber 5 is sealed by the engagement of the distal housing member 12, specifically by an injection needle hub 3 within the distal housing member 12. A fluid transfer sealing member 6 is integrated at the proximal wall 27 of the first medicament chamber 5 for preventing fluid communication between the first medicament chamber 5 and the transfer needle 7. Herein, the transfer needle 7 and the transfer sealing member 6 are collectively referred to as a "medicament transfer feature."

The distal housing member 12 comprises an injection needle 2 coaxially fixed within the injection needle hub 3. Like the transfer needle 7, in other embodiments, coaxial positioning of the injection needle 2 is not necessary. As shown, a sealing cap 18 is removably attached to the distal housing member 12 and prevents contamination of the injection needle 2 before use. In other embodiments the sealing cap 18 may be removably attached to the injection needle 2. The distal housing member 12 and the injection needle hub 3 are at least partially fixed together and both components form a recess 10 for receiving the slidably engaged proximal housing member 11. This engagement allows axial telescopic movement of the distal housing member 12 and the proximal housing member 11. The distal housing member 12 may be fixed to the injection needle hub 3 using any connection mechanism known in the art including threads, press fit, ratchet mechanism, and adhesive.

Figure 1D:
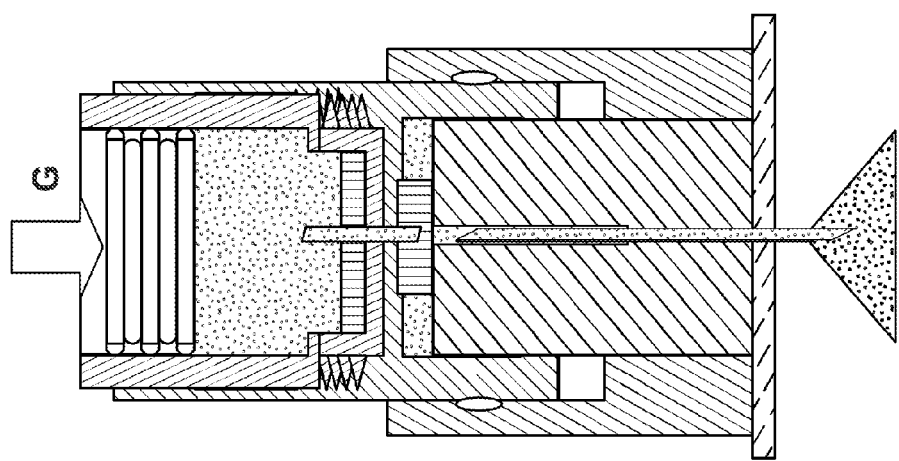
FIG. 1d is a cross-sectional view of the needle assembly of FIG. 1b during a second delivery step.

FIG. 1b is a cross-sectional view of the needle assembly 1 of FIG. 1a connected to a drug delivery device. However, for simplicity, instead of an entire drug delivery device, only a cartridge 13 (shown without a cartridge holder) is illustrated comprising (i) a chamber 14 containing a second medicament 29, (ii) a pierceable septum 15, and (iii) a plunger 30 (also commonly referred to as a "piston," "bung," or "stopper.") The plunger 30 is used to expel the second medicament 29 from the cartridge when driven by conventional drive mechanisms as well known in the art (see FIG. 1d). As shown, the cartridge 13 is connected, via a threaded engagement, to the needle assembly 1 at the mounting portion 9. In actual operation the cartridge 13 may be held by a cartridge holder of a drug delivery device and the cartridge holder or another component of the drug delivery device may attach to the needle assembly 1. Upon attachment of the cartridge 13 to the needle assembly 1, the transfer needle 7 pierces the pierceable septum 15, however, the transfer sealing member 6 in its initial state (the mechanism is explained later) prevents fluid communication between the first medicament chamber 5 and the second medicament chamber 14. As shown in FIG. 1b, the device is ready for use.

In FIG. 1c the injection needle 2 is introduced into a patient (or user) 31 and pressed against the skin of the patient (herein, this is referred to as the "first delivery step" F). When a threshold level of force is applied to the proximal housing member 11 in the distal direction, the distal end of the proximal housing member is able to move past the securing members 25 and the proximal and distal housing members 11, 12 are moved relative to one another in a telescopic manner. This movement causes a displacement of the first medicament 28 out of the first medicament chamber 5, through the injection needle 2, and into the patient 31 (i.e., delivery of the first medicament). During the first delivery step F, the transfer sealing member 6 prevents (i) flow of the first medicament 28 into the second medicament chamber 14 and (ii) flow of the second medicament 29 into the first medicament chamber 5. In other embodiments, the proximal and distal housing members 11, 12 may be configured differently than shown in FIGS. 1a-1d and may be rigidly fixed together such that the housing members 11, 12 do not move relative to one another. In such an embodiment, the injection needle hub 3 may be slidably attached to the distal housing member 12 such that relative movement between the housing members 11, 12 and the injection needle hub 3 causes the first medicament 28 to be delivered.

In FIG. 1d the first delivery step F is complete and the injection needle hub 3, which is at least partially connected to the distal housing member 12, has reached the transfer sealing member 6. In this state no further delivery of the first medicament 28 is possible due to the sealing engagement between the transfer sealing member 6 and injection needle hub 3. Although FIG. 1d shows a small amount of the first medicament 28 still remaining in the first medicament chamber 5, other embodiments may be configured such that all of the first medicament 28 is delivered during the first delivery step F. In a second delivery step G, activation (or actuation) of the drug delivery device (e.g., activation of a dose button of the drug delivery device) forces the plunger 30 distally and increases the pressure on the transfer sealing member 6. This pressure causes the transfer sealing member 6 to open, thus allowing the transfer and delivery of the second medicament 29 to the injection needle 2 and to the patient 31. Although the first and second delivery steps are described discretely, they may be performed in one continuous motion as a single delivery step.

Figure 2B:
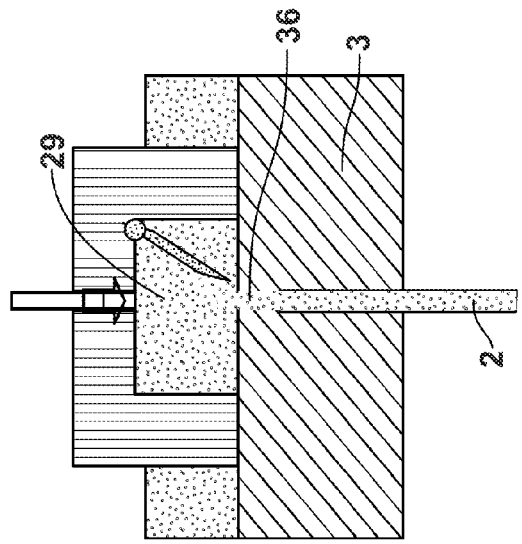
FIG. 2b is a detailed cross-sectional view of the medicament transfer sealing member of FIG. 2a during a second delivery step.

FIGS. 2a and 2b are detailed illustrations of the medicament transfer sealing member 6 of the needle assembly of FIGS. 1a-d during the first and second delivery steps respectively. As shown in FIG. 2a, the transfer sealing member 6 comprises a passageway 33, a unidirectional valve 32, and a transfer sealing member cavity 35. The valve 32 is a pressure activated valve and prevents the second medicament 29 from entering the first medicament chamber 5 and also prevents the first medicament 28 from entering the second medicament chamber 14, until the second delivery step G (i.e., when pressure is applied to the valve 32 in the distal direction). Other embodiments of the transfer sealing member 6 may not include a cavity 35. The fluid pressure (arrows) induced by the first delivery step F helps keeps the unidirectional valve 32 closed during the first delivery step. However, during the second delivery step G (i.e., during activation of the drug delivery device) shown in FIG. 2b, the valve 32 opens due to fluid pressure (arrow) induced by distal movement of the plunger 30 within the second medicament chamber 14. Thus, the second medicament 29 can be transferred and delivered, via the transfer needle 7, the transfer sealing member 6, and the passageway 36, to the injection needle 2 and the user 31.

Figure 3A:
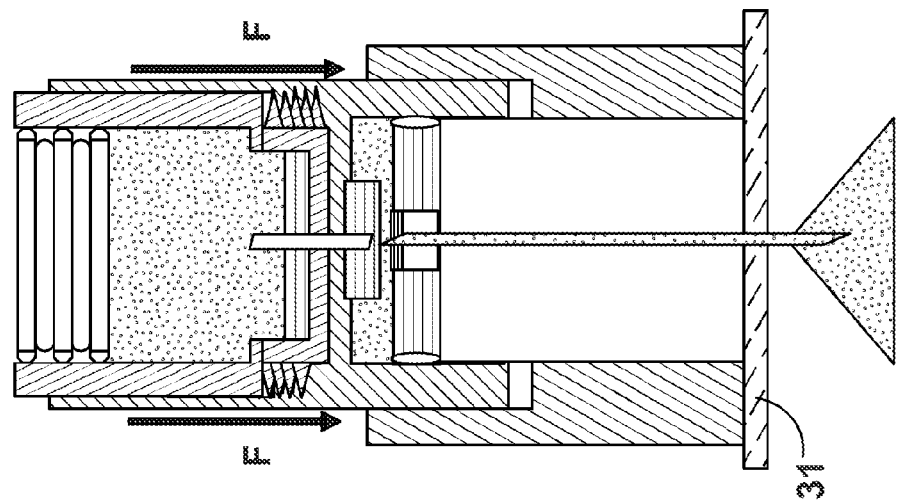
FIG. 3a is a cross-sectional view of another exemplary needle assembly.

FIGS. 3a-d show a second exemplary embodiment of a needle assembly. In general, the overall function and components are similar to those described above with respect to FIGS. 1a-d. The needle assembly 1 shown in FIG. 3a is divided into two major components: a proximal housing member 11 and a distal housing member 12. As shown, both housing members 11, 12 are movably engaged such that they can slide relative to one another. Although not shown, the exemplary needle assembly shown in FIGS. 3a-d may comprise securing members 25 prevent inadvertent relative axial movement between the proximal and distal housing members 11, 12. Each securing member 25 may comprise a cam lock or various other protrusion.

The proximal housing member 11 comprises a mounting portion 9 including threads 8 for attaching the needle assembly 1 to a drug delivery device. Other embodiments may include various other attachment means known in the art such as a snap or ratchet mechanism. As shown, a transfer needle 7 is located coaxially inside the mounting portion 9 and protrudes from the distal wall 26 of the mounting portion 9. Although the transfer needle 7 is shown to be located coaxially inside the mounting portion 9, it may not be coaxially located in other embodiments. The proximal housing member 11 also includes a first medicament chamber 5 containing a first medicament 28. In this embodiment, the distal end of the first medicament chamber 5 is sealed by a moveable bung 4 positioned within the first medicament chamber 5. In other embodiments the moveable bung 4 may only be partially positioned within the first medicament chamber 5. The moveable bung comprises a sealing portion 38 and a pierceable portion 39. The pierceable portion 39 is pierceable by the proximal end 37 of the injection needle 2. A fluid transfer sealing member 6 is integrated at the proximal wall 27 of the first medicament chamber 5 for preventing fluid communication between the first medicament chamber 5 and the transfer needle 7. Herein, the transfer needle 7 and the transfer sealing member 6 are collectively referred to as a "medicament transfer feature."

The distal housing member 12 comprises an injection needle 2 coaxially fixed within an injection needle hub 3, where the injection needle 2 extends from both the proximal and distal ends of the needle hub 3. Like the transfer needle 7, coaxial positioning of the injection needle 2 is not necessary in other embodiments. The distal housing member 12 and the injection needle hub 3 are at least partially fixed together and both components form a recess 10 for receiving the slidably engaged proximal housing member 11. This engagement allows axial telescopic movement of the distal housing member 12 and the proximal housing member 11. The distal housing member 12 may be fixed to the injection needle hub 3 using any connection mechanism known in the art including threads, press fit, ratchet mechanism, and adhesive.

Figure 3B:
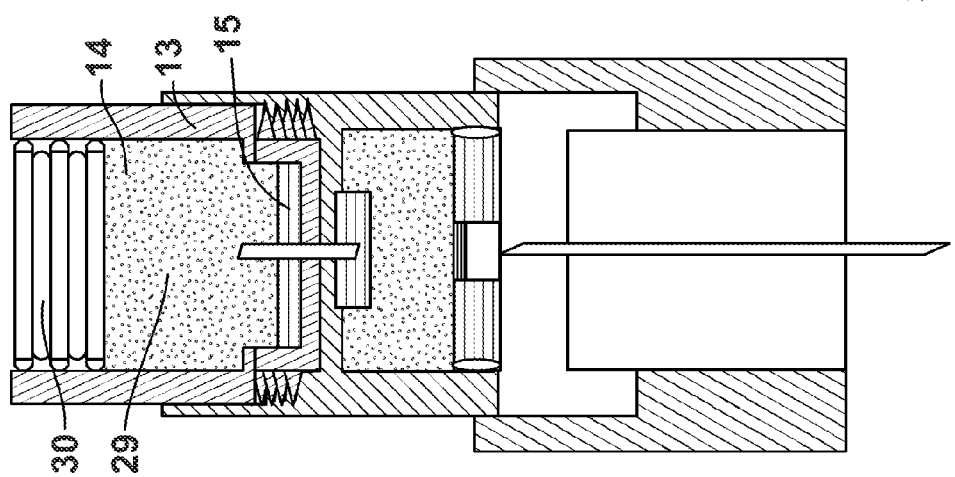
FIG. 3b is a cross-sectional view of the needle assembly of FIG. 3a connected to an exemplary drug delivery device.

FIG. 3b is a cross-sectional view of the needle assembly 1 of FIG. 3a connected to a drug delivery device. However, for simplicity, instead of an entire drug delivery device, only a cartridge 13 (shown without a cartridge holder) is illustrated comprising (i) a chamber 14 containing a second medicament 29, (ii) a pierceable septum 15, and (iii) a plunger 30. The plunger 30 is used to expel the second medicament 29 from the cartridge when driven by conventional drive mechanisms known in the art (see FIG. 1d). As shown, the cartridge 13 is connected, via a threaded engagement, to the needle assembly 1 at the mounting portion 9. In actual operation the cartridge 13 may be held by a cartridge holder of a drug delivery device and the cartridge holder or another component of the drug delivery device may attach to the needle assembly 1. Upon attachment of the cartridge 13 to the needle assembly 1, the transfer needle 7 pierces the pierceable septum 15, however, the transfer sealing member 6 in its initial state (as will be explained) prevents fluid communication between the first medicament chamber 5 and the second medicament chamber 14. As shown in FIG. 3b, the device is ready for use.

Figure 3C:
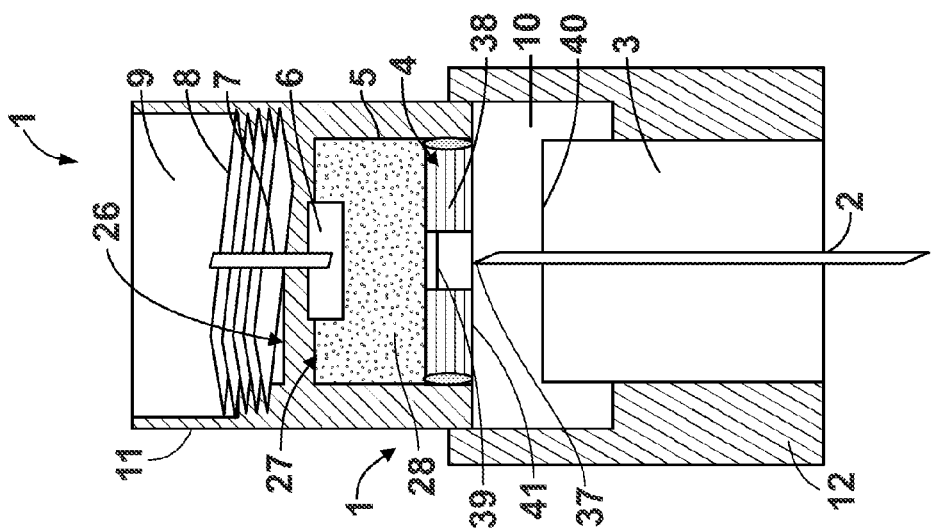
FIG. 3c is a cross-sectional view of the needle assembly of FIG. 3b during a first delivery step.

In FIG. 3c the injection needle 2 is introduced into a patient 31 and pressed against the skin of the patient (this is referred to as the "first delivery step" F). When a threshold level of force is applied to the proximal housing member 11 in the distal direction, the proximal and distal housing members 11, 12 are moved relative to one another in a telescopic manner. During the first delivery step F, a first relative axial movement between the proximal and distal housing members 11, 12 causes the injection needle 2 to pierce the bung 4 at the pierceable portion 39. During a second and further relative axial movement between the proximal and distal housing members 11, 12, the bung 4 is displaced thus leading to discharge of the first medicament 28 out of the first medicament chamber 5, through the injection needle 2, and into the patient 31 (i.e., delivery of the first medicament). During the first delivery step F, the transfer sealing member 6 prevents (i) flow of the first medicament 28 into the second medicament chamber 14 and (ii) flow of the second medicament 29 into the first medicament chamber 5.

Figure 3D:
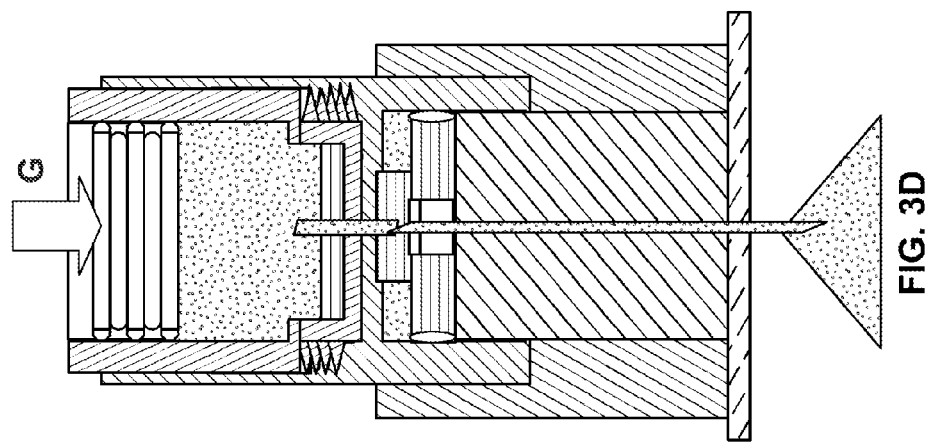
FIG. 3d is a cross-sectional view of the needle assembly of FIG. 3b during a second delivery step.

In FIG. 3d the first delivery step F is complete and the bung 4 has reached the transfer sealing member 6. In this state no further delivery of the first medicament 28 is possible due to the sealing engagement between the transfer sealing member 6 and the bung 4. Although FIG. 3d shows a small amount of the first medicament 28 still remaining in the first medicament chamber 5, other embodiments may be configured such that all of the first medicament 28 is delivered during the first delivery step F. In a second delivery step G, activation (or actuation) of the drug delivery device (e.g., activation of a dose button of the drug delivery device) forces the plunger 30 distally and increases the pressure on the transfer sealing member 6. This pressure causes the transfer sealing member 6 to open, thus allowing the transfer and delivery of the second medicament 29 to the injection needle 2 and to the patient 31. Although the first and second delivery steps are described discretely, they may be performed in one continuous motion as a single delivery step.

Figure 4A:
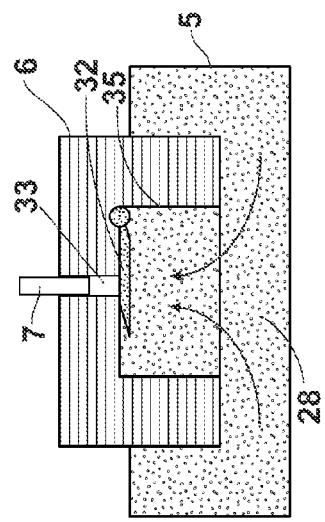
FIG. 4a is a detailed cross-sectional view of an exemplary medicament transfer sealing member of the needle assembly of FIG. 3b during a first delivery step, where the transfer sealing member comprises a valve.
Figure 4B:
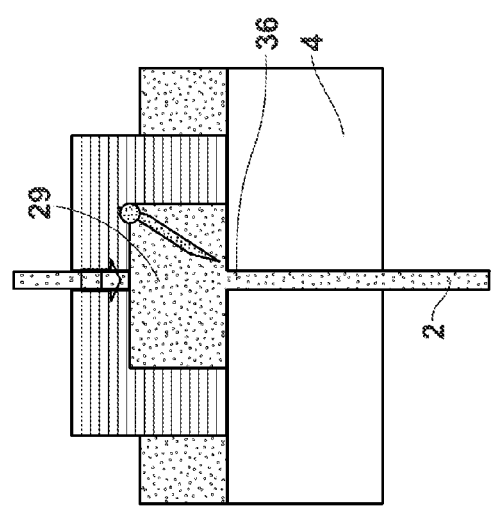
FIG. 4b is a detailed cross-sectional view of the medicament transfer sealing member of FIG. 4a during a second delivery step.

FIGS. 4a and 4b are detailed illustrations of the medicament transfer sealing member 6 of the needle assembly of FIGS. 3a-d. The sealing member 6 shown is substantially similar to the one described with respect to FIGS. 2a and 2b and therefore, the above description with regard to FIGS. 2a and 2b is applicable here and will not be repeated. The only difference being that in FIG. 4b the bung 4 abuts the transfer sealing member 6 instead of the injection needle hub 3 abutting the transfer sealing member 6 as in FIG. 2b.

Figure 5D:
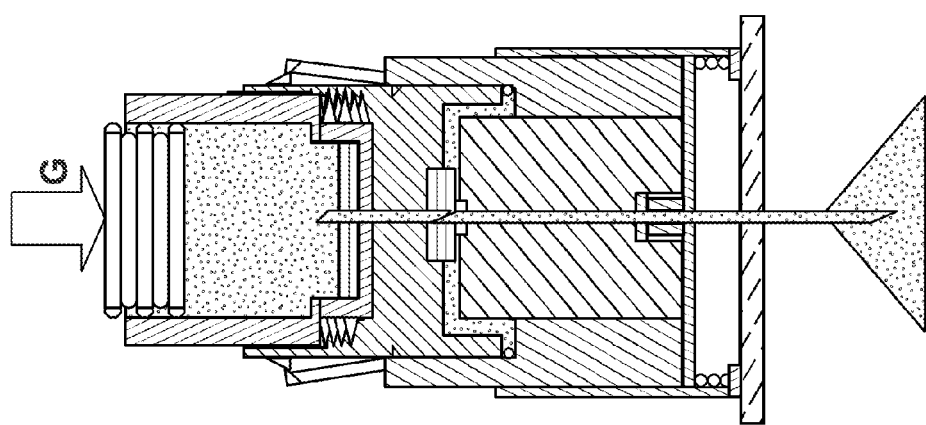
FIG. 5d is a cross-sectional view of the needle assembly of FIG. 5b during a second delivery step.

FIGS. 5a-d show a third exemplary embodiment of a needle assembly. In general, the overall function and components are similar to that described above with respect to FIGS. 1a-d. The needle assembly 1 shown in FIG. 5a is divided into two major components: a proximal housing member 11 and a distal housing member 12. As shown, both housing members 11, 12 are movably engaged such that they can slide relative to one another. Unlike the embodiments shown in FIGS. 1a-d and 3a-d, the needle assembly shown in FIGS. 5a-d includes a needle shield 16.

In its neutral state, the needle shield 16 covers the distal end of the injection needle 42. The needle shield 16 comprises a compression spring 17 arranged to bias the needle shield 16 into the outmost extended position (before and after use). The injection needle 2 is movably attached to the needle hub 3 by a slidable collar 23. The proximal end of the injection needle 37 is positioned below the proximal surface of the needle hub 40 and is separated from the first medicament chamber 5 by a pierceable hub sealing member 45. A needle slide 46 is arranged near the center of the shield 16 and is connected to the shield via bars 47. In other embodiments, a different connection means may be used to attach the needle slide 46 to the shield 16. For instance, a plate or flange extending from the inner walls of the shield 16 may connect the needle slide 46 to the shield 16. To avoid inadvertent relative axial movement between the proximal and distal housing members 11, 12, a blocking mechanism 48 comprising a blocking member 22 and a blocking recess 24 is introduced.

Axial movement of the proximal housing member 11 towards the distal housing member 12 is blocked by the blocking member 22, which is engaged in the blocking recess 24. The blocking member 22 may be made of a flexible and/or resilient material or of a rigid material. As shown, the blocking member 22 is connected to the distal housing member 12 and the blocking recess 24 is located on the outer surface of the proximal housing member 11. However, in other embodiments the blocking member 22 may be connected to the proximal housing member 11 and the blocking recess 24 may be located on the outer surface of the distal housing member 12. The blocking member 22 may be pivotably connected to the distal housing member 12.

The shield 16 comprises a slidably arranged unblocking member 21. The unblocking member 21 may be triangular in shape as shown best in FIG. 5a. The slidably arranged unblocking member 21 is configured such that proximal movement of the shield 16 during use of the needle assembly 1 leads to unblocking of the proximal and distal housing members 11, 12 at a certain position. As the shield 16 moves in the proximal direction during use of the needle assembly 1, the unblocking member 21, which may be part of the shield 16 or perhaps attached to the shield 16, is forced in the proximal direction. When the unblocking member 21 contacts the proximal end of the blocking member 22, the blocking member is disengaged from the recess 24 and relative axial movement between the proximal and distal housing members 11, 12 is enabled.

FIG. 5b is a cross-sectional view of the needle assembly 1 of FIG. 5a connected to a drug delivery device. During use, the shield 16 is pressed against the skin (indicated by arrows E) of the patient 31 and as a result, the shield 16 retracts (i.e., moves proximally) until the injection needle slide 46 engages the needle collar 23 which attaches the injection needle 2 to the needle hub 3. Additional proximal shield movement leads to parallel movement of the needle 2 in the proximal direction such that the pierceable hub sealing member 45 is pierced by the proximal end of the injection needle 37. Thus, fluid communication between the injection needle 2 and the first medicament chamber 5 is established. At the same time, this proximal movement of the shield 16 releases the blocking mechanism 48.

After the release of the blocking mechanism 48, the medicament delivery is carried out in the same way as described with respect to FIGS. 1a-d. FIG. 5c shows the first delivery step F whereby the first medicament 28 is delivered and FIG. 5d shows the second delivery step G whereby the second medicament 29 is delivered. After the first and second medicaments 28, 29 are delivered, the injection needle 2 is removed from the patient 31 and the spring 17 urges the shield 16 again into the outmost extended position, thus covering the distal end of the injection needle 42. In another embodiment a mechanism may be introduced to prevent reuse of the needle assembly 1. For example, a locking mechanism such as one known in the art may be introduced that locks the shield 16 in its outermost distal position (i.e., position shown in FIG. 5a) after use.

Figure 6A:
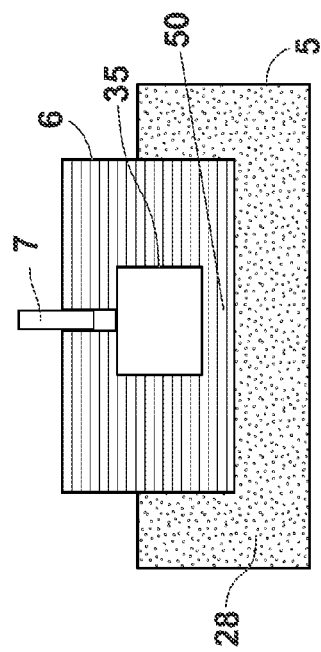
FIG. 6a is a detailed cross-sectional view of an exemplary medicament transfer sealing member of an exemplary needle assembly during a first delivery step, where the transfer sealing member comprises a sealing surface.
Figure 6B:
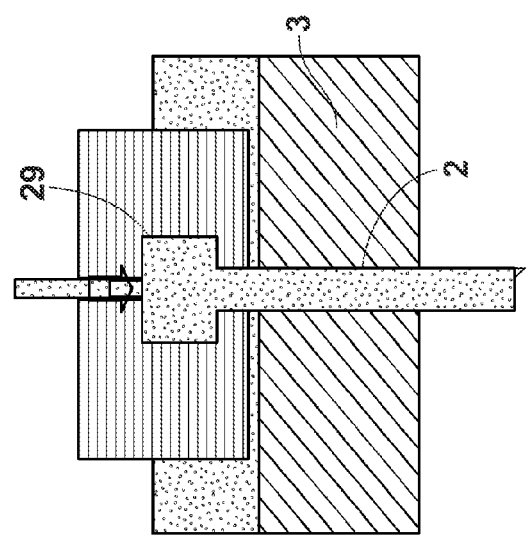
FIG. 6b is a detailed cross-sectional view of the medicament chamber transfer sealing member of FIG. 6a during a second delivery step.

FIGS. 6a and 6b are detailed illustrations of an exemplary medicament transfer sealing member 6 that may be used with any of the needle assembly embodiments described herein during the first and second delivery steps respectively. As shown in FIG. 6a, the transfer sealing member 6 comprises a transfer sealing member cavity 35 and a sealing surface 50. The sealing surface 50 prevents the second medicament 29 from entering the first medicament chamber 5 and also prevents the first medicament 28 from entering the second medicament chamber 14 during the first delivery step F. Other embodiments of the transfer sealing member 6 may not include a cavity 35. In this embodiment, prior to the second delivery step G, the injection needle 2 must pierce the sealing surface 50 so that the second medicament 29 can be delivered. The injection needle 2 may pierce the sealing surface 50 near the end of the first delivery step F.

Figure 7A:
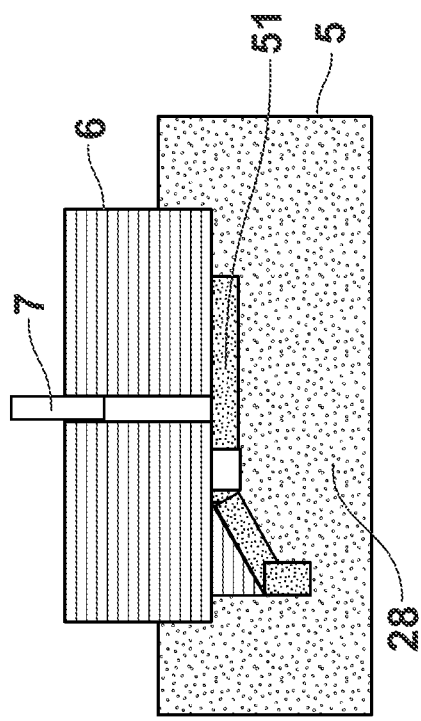
FIG. 7a is a detailed cross-sectional view of an exemplary medicament chamber transfer sealing member during a first delivery step, where the transfer sealing member comprises a slider.
Figure 7B:
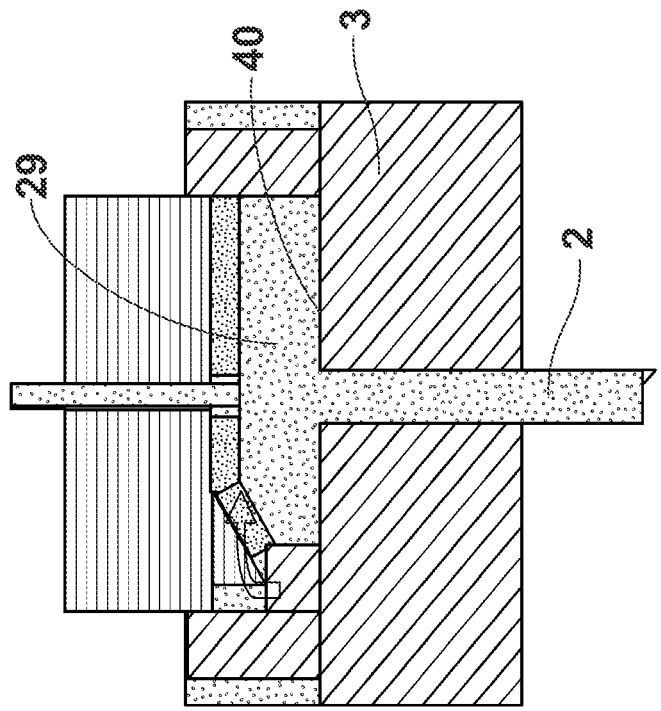
FIG. 7b is a detailed cross-sectional view of the medicament chamber transfer sealing member of FIG. 7a during a second delivery step.

FIGS. 7a and 7b illustrate another exemplary medicament transfer sealing member 6 that may be used with any of the needle assembly embodiments described herein during the first and second delivery steps respectively. As shown in FIG. 7a, the transfer sealing member 6 comprises a slider 51 in its closed position (i.e., no fluid communication between the first and second medicament chambers 5, 14). In this embodiment, the proximal needle hub surface 40 is modified (mechanically or electronically) to force the slider 51 into its open configuration (see FIG. 7b) during the second delivery step G, thus providing fluid communication between the injection needle 2 and the second medicament chamber (not shown in FIGS. 7a and 7b).

Various exemplary embodiments have been described above. Those skilled in the art will understand, however, that changes and modifications may be made to those embodiments without departing from the scope of the claims. For instance, other embodiments of a needle assembly may include additional features instead of and/or in addition to those depicted in FIGS. 1a-7b. For example, although various exemplary transfer sealing members have been described, other transfer sealing members known in the art may be used (e.g., mechanical or electronic valves, other shutter solutions such as a rotating disc with closed and opened configuration, etc.). Additionally, other embodiments may include some but not all of the features depicted in the figures.

The invention claimed is:

1. A needle assembly attachable to a drug delivery device for delivering two or more medicaments, the needle assembly comprising:
 a proximal housing member comprising a medicament chamber pre-filled with a single dose of a first medicament, wherein the proximal housing member is configured to attach to the drug delivery device containing a second medicament, wherein the medicament chamber is pre-filled with the single dose of the first medicament before the needle assembly is attached to the drug delivery device, and further comprising an axially moveable bung positioned at least partially within the medicament chamber, wherein a distal end of the medicament chamber is sealed by the moveable bung, and a distal housing member movably engaged with the proximal housing member, such that relative axial movement between the proximal and distal housing members causes the volume of the medicament chamber to be reduced and the single dose of the first medicament to enter an injection needle arranged at the distal housing member and to be delivered; and a medicament transfer feature located in the proximal housing member for transferring a dose of the second medicament from the drug delivery device to the injection needle of the needle assembly, said medicament transfer feature comprising a transfer needle to establish fluid communication between the medicament in the drug delivery device and the needle assembly and being switchable between a first and a second state, wherein the drug delivery device comprises multiple doses of the second medicament, wherein in the first state the medicament transfer feature is configured to prevent fluid communication between the first and the second medicament, wherein in the first state the proximal housing member and the movable bung are configured to move axially relative to the distal housing member and distally relative to the injection needle, wherein in the subsequent second state the medicament transfer feature is configured to transfer the second medicament from the drug delivery device to the injection needle of the needle assembly.

2. The needle assembly of claim 1, wherein fluid communication between the first and the second medicament is established upon activation of the drug delivery device.

3. The needle assembly of claim 1, further comprising an injection needle hub attached to the distal housing member, wherein the injection needle is coaxially fixed within the injection needle hub.

4. The needle assembly of claim 1, wherein the medicament transfer feature further comprises a transfer sealing member configured to prevent fluid communication between the medicament chamber and a second medicament chamber.

5. The needle assembly of claim 1, further comprising at least one securing member for preventing inadvertent relative axial movement between the proximal and distal housing members.

6. The needle assembly of claim 5, wherein the at least one securing member comprises at least one cam lock.

7. The needle assembly of claim 1, wherein the distal housing member movably engaged with the proximal housing member comprises the distal housing member slidably engaged with the proximal housing member.

8. The needle assembly of claim 1, wherein the moveable bung comprises (i) a pierceable portion pierceable by a proximal end of the injection needle and (ii) a sealing portion.

9. The needle assembly of claim 8, wherein a first relative axial movement between the proximal and distal housing members results in the proximal end of the injection needle piercing the pierceable portion of the moveable bung, and wherein a second relative axial movement between the proximal and distal housing members results in the moveable bung moving in the proximal direction such that the first medicament is delivered.

10. A method of delivering at least two medicaments, the method comprising:
providing the needle assembly of claim 1;
attaching the needle assembly to a drug delivery device containing a second medicament;
inserting the injection needle into a user;
axially moving the proximal and distal housing members of the needle assembly relative to one another such that the single dose of the first medicament is delivered to the user; and
activating the drug delivery device such that the single dose of the multiple doses of the second medicament is delivered to the user by transferring the single dose of the second medicament from the drug delivery device to the injection needle of the needle assembly.

11. A drug delivery device for delivering two or more medicaments, the drug delivery device comprising:
(i) a dose setting mechanism;
(ii) a medicament cartridge; and
(iii) the needle assembly of claim 1.

12. The drug delivery device of claim 11 wherein the two or more medicaments comprise a first medicament and a second medicament, wherein the first medicament is different from the second medicament.

13. The needle assembly of claim 1, wherein the moveable bung is pierced at a piercable portion for reduction of the volume of the medicament chamber.

* * * * *

UNITED STATES PATENT AND TRADEMARK OFFICE
CERTIFICATE OF CORRECTION

PATENT NO. : 9,950,113 B2  
APPLICATION NO. : 13/881977  
DATED : April 24, 2018  
INVENTOR(S) : Beate Franke and Zdenek Cerman Page 1 of 1

It is certified that error appears in the above-identified patent and that said Letters Patent is hereby corrected as shown below:

On the Title Page

Item [57], Line 4, after "or" insert -- more --;

In the Claims

Column 16, Line 48, Claim 13, delete "piercable" and insert -- pierceable --.

Signed and Sealed this  
Twenty-ninth Day of January, 2019

Andrei Iancu  
*Director of the United States Patent and Trademark Office*